US00PP31445P2

(12) United States Plant Patent
Stoppel

(10) Patent No.: US PP31,445 P2
(45) Date of Patent: Feb. 18, 2020

(54) CHERRY TREE NAMED 'PRIM 21'

(50) Latin Name: ***Prunus avium* L.**
Varietal Denomination: Prim 21

(71) Applicant: Peter Stoppel, Kressbronn (DE)

(72) Inventor: Peter Stoppel, Kressbronn (DE)

(73) Assignee: Cerasina GmbH, Kressbronn (DE)

( * ) Notice: Subject to any disclaimer, the term of this patent is extended or adjusted under 35 U.S.C. 154(b) by 0 days.

(21) Appl. No.: 16/501,496

(22) Filed: Apr. 18, 2019

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
CPC ..... A01H 5/08; A01H 6/74
See application file for complete search history.

*Primary Examiner* — Annette H Para
(74) *Attorney, Agent, or Firm* — The Webb Law Firm

(57) ABSTRACT

A new and distinct variety of sweet cherry tree that produces heart-shaped and dark red colored fruits with very firm fruit flesh.

2 Drawing Sheets

Botanical classification: *Prunus avium* L.
Varietal denomination: 'Prim 21'.

BACKGROUND OF THE INVENTION

The present invention comprises a new and distinct variety of sweet cherry tree, botanically known as *Prunus avium* L., and referred to by the varietal name 'Prim 21'. The new variety was discovered in Baden-Wuerttemberg, Germany as the result of planned breeding between cherry tree variety named 'PC 7144-7', known and marketed as "Tieton" (female parent, U.S. Plant Pat. No. 8,051), and an unnamed and unpatented cherry tree variety as the male parent. The purpose of the breeding program was to produce high quality fruits with an early ripening time. The new variety was first asexually reproduced via cuttings in Baden-Wuerttemberg, Germany in 2006. The new variety has been trial and field tested and has been found to retain its distinctive characteristics and remain true to type through successive propagations. The present invention has not been evaluated under all possible environmental conditions. The phenotype may vary with variations in environment without a change in the genotype of the plant.

The new variety is similar to both parental varieties in exhibiting a dark red fruit color, high fruit firmness, and medium early blooming time. The new variety differs from its parental varieties in tree habit, fruit ripening time, and fruit shape. When specifically compared to "Tieton", 'Prim 21' has similar S-alleles/S3S9, but exhibits a medium strong and wide tree habit versus the upright and strong tree habit of "Tieton", a fruit ripening time that is 8 days earlier than "Tieton", and fruit that is more heart-shaped than "Tieton". When compared to cherry tree variety named 'Burlat' (unpatented), the fruits of 'Prim 21' are more firm and heart-shaped versus the round shape of 'Burlat', and 'Prim 21' exhibits a weaker growth habit than 'Burlat'. Further, the following characteristics distinguish the new variety from other varieties known to the breeder:

1. 'Prim 21' exhibits a much darker fruit color than 'Bellise' (unpatented);

2. 'Prim 21' exhibits a fruit ripening time that is 10 days earlier than 'Grace Star' (unknown patent protection); and
3. 'Prim 21' exhibits a flowering time that is 8 days earlier than 'Kordia' (unpatented).

DESCRIPTION OF THE DRAWINGS

The accompanying photographic drawings illustrate the new variety at approximately 7 years of age with the color being as nearly true as is possible with color illustrations of this type.

DETAILED BOTANICAL DESCRIPTION

Figure 1:
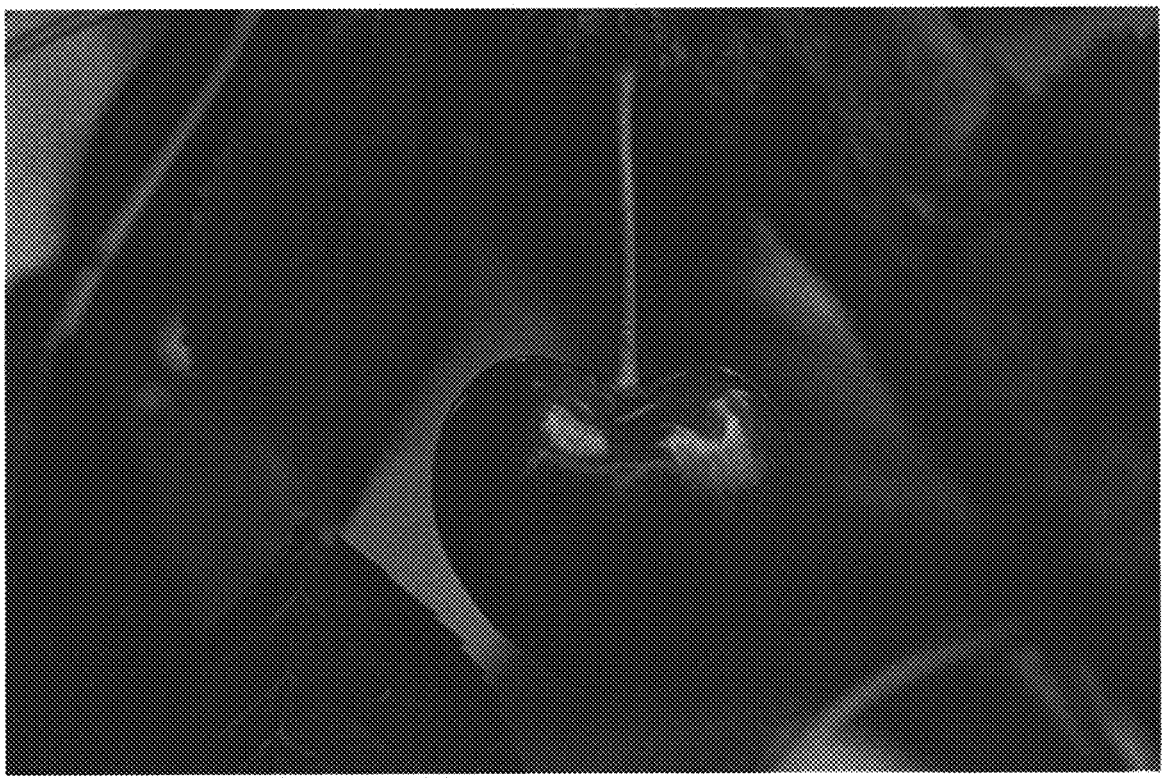
FIG. 1 is a close-up photograph of the fruit of 'Prim 21'.
Figure 2:
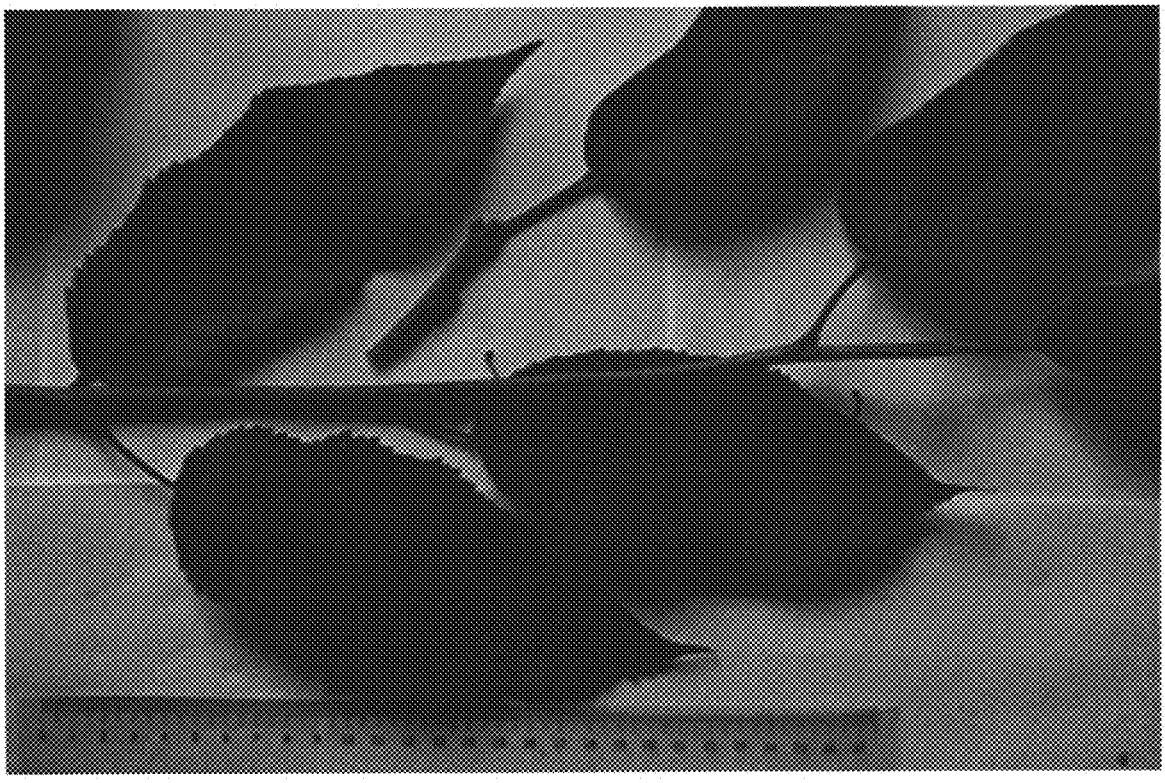
FIG. 2 is a close-up photograph of the leaves of 'Prim 21'.

The following detailed description sets forth the characteristics of the new variety. The data which defines these characteristics were collected by asexual reproductions via cuttings carried out in Kressbronn, Germany. The new variety was grown outside under natural soil conditions. The color readings were taken outside in natural daylight and the variety was approximately 7 years old when described. Color references are primarily to The R.H.S. Colour Chart of The Royal Horticultural Society of London, except where terms of ordinary significance are used.

TREE

Height: 3.0 m.
Width: 2.0 m, measured at 10.0 cm above ground level.
Vigor: Medium.
Density: Medium.
Form: Upright spread with a medium level of lateral branching.
Growth type: Spreading.
Bearing: Annually on spurs, with 3-4 bud positions located at the base of one-year old shoots.

Disease/pest resistance or susceptibility: Nothing unusual noted to date.

Trunk:

*Size*.—Medium.

*Bark color*.—RHS 199A.

*Surface texture*.—Smooth, with prominent lenticels.

*Lenticels*.—Length: 1.0-2.0 cm. Width: 0.5 cm. Density: Medium. Color: RHS 167A.

Branches:

*Diameter*.—0.5-1.5 cm.

*Surface texture*.—Of a typical sweet cherry tree; Smooth, with lenticels present.

*Color*.—RHS 164A.

*Form*.—Of a typical sweet cherry tree.

*Average angle*.—60-75 degrees.

*Bud arrangement*.—Of a typical sweet cherry tree.

*Lenticels*.—Length: About 1.0 mm. Width: About 1.0 mm. Shape: Rounded. Density: Few and scattered. Color: RHS 161B.

Leaves:

*Length*.—16.0-19.0 cm.

*Width*.—7.0-8.0 cm.

*Form*.—Thin and narrow.

*Shape*.—Lanceolate.

*Texture*.—Soft, with a crisp feeling.

*Thickness*.—Medium.

*Apex*.—Acute.

*Base*.—Rounded.

*Margin*.—Regularly serrate.

*Color*.—Upper surface: RHS 141A. Lower surface: RHS 142D.

*Petiole*.—Shape: Narrow. Length: 3.5-4.5 cm. Diameter: About 2.0 mm. Color: Adaxial surface: RHS 59A. Abaxial surface: RHS 149C. Venation: Type: Pinnate. Color: RHS 154D.

FLOWERS

Flower buds:

*Color*.—Reddish.

*Length*.—About 1.0 cm.

*Width*.—Under 1.0 cm.

*Pedicel*.—Length: 12.0 mm. Diameter: 0.4 mm.

Flowers:

*Bloom timing*.—Toward the end of April in Kressbronn, Germany.

*Blooming period*.—Medium to early in the season, similar to 'Burlat'.

*Number of flowers per raceme*.—3 to 7.

*Pollination requirements*.—Cross-pollination needed.

*Petals*.—Number: 5. Length: 15.0 mm. Width: 12.0 mm. Shape: Oval. Apex: Slightly obcordate. Margin: Slightly undulate. Texture: Soft. Color: RHS 155D (both surfaces).

*Sepals*.—Length: 5.0-7.0 mm. Width: About 5.0 mm. Shape: Conical. Margin: Regular. Color: RHS 143C (both surfaces).

Reproductive organs:

*Stamens*.—Number per flower: 4 to 5. Filament: Length: 11.0 mm. Width: 0.1 mm.

*Anthers*.—Shape: Kidney. Length: 0.6 mm. Color: RHS 13B.

*Pollen*.—Color: RHS 13B. Amount: Plentiful.

*Pistil length*.—12.0 mm.

*Style*.—Length: 4.0-6.0 mm. Color: RHS 143C.

*Stigma*.—Shape: Oval. Color: Green.

FRUIT

Fruit:

*Maturity when described*.—Eating maturity.

*Size*.—Diameter: 2.7-3.0 cm. Length: 3.1 cm.

*Skin*.—Thickness: Medium. Texture: Smooth. Tendency to crack: Not prone to cracking from rain. Color: RHS 53A.

*Flesh*.—Aroma: Pleasant. Color: RHS 53A. Texture: Very firm. Eating quality: Good.

*Seeds*.—Number per fruit: 1. Length: 1.2 cm. Breadth: 0.6-0.8 cm. Form: Round. Color: Light brown.

*Stem*.—Length: 3.0-3.5 cm. Width: 0.1 cm. Color: Light green.

I claim:

1. A new and distinct variety of cherry tree, as is herein illustrated and described.

* * * * *